(12) United States Patent
Yoneda et al.

(10) Patent No.: US 8,512,744 B2
(45) Date of Patent: Aug. 20, 2013

(54) SUSTAINED RELEASE MICROPELLETS AND PROCESS FOR PRODUCING THE SAME

(75) Inventors: Fumio Yoneda, Matsubara (JP); Fumiya Hamano, Matsubara (JP); Eisaku Kitano, Matsubara (JP); Tetsuya Hosono, Matsubara (JP)

(73) Assignee: Fujimoto Co., Ltd., Osaka (JP)

( * ) Notice: Subject to any disclaimer, the term of this patent is extended or adjusted under 35 U.S.C. 154(b) by 1498 days.

(21) Appl. No.: 11/889,744

(22) Filed: Aug. 16, 2007

(65) Prior Publication Data

US 2009/0011034 A1 Jan. 8, 2009

Related U.S. Application Data

(63) Continuation of application No. 10/486,898, filed as application No. PCT/JP02/08245 on Aug. 12, 2002, now abandoned.

(30) Foreign Application Priority Data

Aug. 17, 2001 (JP) ................................. 2001-248426

(51) Int. Cl.
*A61K 9/26* (2006.01)
*A61K 9/20* (2006.01)
*A61K 9/22* (2006.01)

(52) U.S. Cl.
USPC ............................ 424/464; 424/468; 424/470

(58) Field of Classification Search
USPC ........................................................ 424/470
See application file for complete search history.

(56) References Cited

U.S. PATENT DOCUMENTS

| | | | |
|---|---|---|---|
| 4,713,248 A | 12/1987 | Kjornaes et al. | |
| 4,777,049 A | 10/1988 | Magruder et al. | |
| 5,026,560 A | 6/1991 | Makino et al. | |
| 5,229,135 A * | 7/1993 | Philippon et al. | 424/494 |
| 5,460,828 A | 10/1995 | Santus et al. | |
| 5,576,022 A * | 11/1996 | Yang et al. | 424/472 |
| 6,077,533 A | 6/2000 | Oshlack et al. | |

FOREIGN PATENT DOCUMENTS

| | | |
|---|---|---|
| EP | 0 238 189 | 9/1987 |
| EP | 0 277 741 | 8/1988 |
| EP | 0 339 811 | 11/1989 |
| EP | 0 381 181 | 8/1990 |
| EP | 711152 | 5/1996 |
| JP | 58-35110 | 3/1983 |
| JP | 58035110 | 3/1983 |
| JP | 59-44311 | 3/1984 |
| JP | 7-89849 | 4/1995 |

OTHER PUBLICATIONS

Particle Size dated May 15, 2002.*

* cited by examiner

*Primary Examiner* — Michael G Hartley
*Assistant Examiner* — Melissa Perreira
(74) *Attorney, Agent, or Firm* — Wenderoth, Lind & Ponack, L.L.P.

(57) ABSTRACT

Sustained release micropellets showing a stable controlled-release of a drug without being affected by the changes in pH value etc., characterized by being produced by coating core particles with a layer containing a water-soluble drug and further forming a film layer containing a water-insoluble polymer compound and a plasticizer on the thus obtained particles, locating a water-soluble filler layer between the water soluble drug-containing layer and the film layer, and having an average particle size of 300 μm or less; medicinal compositions containing these micropellets; and a process for producing the same.

27 Claims, 2 Drawing Sheets

SUSTAINED RELEASE MICROPELLETS AND PROCESS FOR PRODUCING THE SAME

This is a continuation of Ser. No. 10/486,898, filed Feb. 17, 2004 now abandoned, which is a U.S. national stage of International Application No. PCT/JP02/08245 filed Aug. 12, 2002.

FIELD OF THE INVENTION

The present invention relates to sustained release micropellets with controlled release of a water-soluble drug, medicinal compositions containing these micropellets, and a process for producing the same.

BACKGROUND ART

A sustained release preparation with controlled release of a drug can maintain the blood concentration of the drug within the therapeutically effective range throughout a considerably long period of time. That is, the sustained release preparation, as compared with usual preparations, is more suitable for improvement of the therapeutic effectiveness by maintaining the effective blood concentration of the drug and also for improvement of patients' QOL (quality of life) by suppression of adverse reactions caused by unnecessary increase or drastic change of the blood concentration and by maintenance of patients' compliance. Thus sustained release preparations have long been studied from various viewpoints.

For example, sustained release oral preparations such as spansules, spantalontabs, repetabs, etc. are known. However preparations with a large diameter such as tablets and capsules may be undesirable for oral administration in the aged, children, or patients with difficulty in swallowing. For easier oral administration of a sustained release preparation to these people, the preparation should desirably be composed of as small as possible units that are still capable of sustained release and be able to be formulated as a suspension, paste, or syrup as needed. Such a sustained release preparation composed of small units is suitable also for easy adjustment of the dose when the necessary dose varies according to the difference in sensitivity, tolerance, progression of diseases, etc.

Microcapsule preparations are known among sustained release preparations having an average particle size of 200 μm or less. For example, a preparation of microcapsules produced by the drying-in-liquid method has been disclosed in Japanese Unexamined Patent Publication No. 109711/1986 etc. Production of microcapsules, as compared with production of particles by layering or coating, is industrially disadvantageous in respect of apparatus, equipments, factors to be controlled, etc. In case of microcapsules containing a water-soluble drug where water or an aqueous solvent is charged in the capsule, problems such as softening of capsules due to miscibility of the water with the coating film during capsulation and/or water migration after capsulation and difficulty in prevention of the influence of water on the content along time-course, are apt to arise. In addition, when the organic solvents are used in the production of the microcapsules, attention should be paid to safety and environmental problems such as residue, inflammability, exhaust gas of the organic solvents.

"Layering" means a technique for formation of granulation product containing a drug, etc. by coating the surface of core particles with the drug alone or in combination with a filler, binder, etc. "Coating" is a technique for formation of a layer consisting of fat or fatty oil, a polymer, etc. on the surface of solid particles such as core particles or granulation product whereby drug-release control, contribution to stability, or masking of unpleasant odor, taste, etc. is attained. Layering methods include granulation by spraying a solution, suspension, or dispersion of the coating ingredients followed by drying, and granulation by addition, adhesion, and binding of the coating ingredients while spraying a binder-containing solution followed by drying. Coating methods include spraying of a solution, suspension, or dispersion of the film components followed by drying.

A persistent severe pain disturbs patients' daily activities due to insomnia, loss of appetite, etc. may cause, in physical conditions, loss of strength, general prostration, and even aggravation of the underlying disease, and in mental conditions, various adverse influences such as fear, anxiety, and apprehension of occurrence of neurological symptoms such as depression. Therefore resolution or alleviation of pain has been the great important problems as well as treatment of the underlying disease.

A number of drugs are now available as analgesic agents, among which morphine, an opioid analgesic agent, is representative. The analgesic effect of morphine is remarkable. Morphine is included in the list of basic drugs of The World Health Organization (WHO) for patients suffering from cancer with persistent severe pain, and WHO recommends oral administration whenever possible, intrarectal administration when oral administration is impossible, injection when intrarectal administration is also impossible, dose adjusted for a patient, regular administration at specified time intervals, efforts to prevent adverse reactions due to the drug as far as possible, consideration of patients' mental state, etc. Morphine, having a short half-life, requires frequent administration; for instance, every 4 hours even while sleeping at night is necessary for persistent efficacy, and this has posed problems in patients' compliance and QOL.

For solving these problems, sustained release preparations of morphine have been developed, including MS CONTIN tablet (trade name by Shionogi & Co. Ltd.) and capsules and sticks of KADIAN (trade name by Faulding Co.) which are prepared by matrix formation with a water-insoluble polymer compound or by film coating. MS Contin tablets are film-coated tablets of about 7.1 mm in diameter and about 4.4 mm in thickness, prepared by coating with a higher alcohol film the granules where morphine sulfate is formed into matrix with a gel-forming polymer compound such as hydroxyethylcellulose. MS Contin tablets are sustained release tablets as the basic unit designed so that morphine in the tablet is released gradually by water that has penetrated through the higher alcohol film into the tablet to maintain the analgesic effect by twice-a-day administration. However, oral administration is difficult in some cases and fine adjustment of the dose is impossible because one tablet is the basic unit of the sustained release. In addition, because the tablets, when broken, lose their sustained releaseability, much morphine may be released at a time when the patient has crunched the tablet in the mouth, so that the blood concentration may be increased rapidly to cause serious adverse reactions such as dyspnea and disturbance of consciousness. KADIAN is a preparation of which units are sustained release pellets (particles) of 1.0 to 1.7 mm in average particle size. These sustained release pellets are filled in hard capsules to prepare KADIAN capsules (No. 2 or No. 4 capsules), or divided and packaged to prepare KADIAN sticks. The mechanism of sustained release of KADIAN is pH-dependent control of release of morphine by the coating of the hybrid type consisting of a water-insoluble polymer compound, an acid-soluble polymer compound, and an enteric polymer compound.

However, in patients with decreased digestive function, sustained release of the type that is dependent on the pH in the digestive tract may not be effective enough. Furthermore, there are some additional disadvantages in respect of easiness of administration, such as bulkiness of preparations with high content of morphine, and being unable to be prescribed in the form of a suspension, paste, or syrup by addition of an adequate amount of water, an aqueous solution etc. before administration.

In general, during layering or coating of core particles or granulation products having an average particle size of 300 µm or less, cohesion or scattering of the particles or granulation products is apt to occur, and the specific surface area becomes large, so that it is difficult to obtain stable sustained release preparations when the amount of the coating agent is 50% by weight or less of the amount of the core particles or solid particles. Japanese Unexamined Patent Publication No. 2001-106627 has disclosed sustained release granules having an average particle size of 50 to 250 µm that can be prepared more easily than microcapsules and without use of any organic solvents and can be formulated into fine granules or dry syrup preparations where weight ratio of the water-insoluble polymer compound is 40 to 150% of that of the active ingredient, theophylline. However, as theophylline is slightly soluble in water, the ability of granules to sustain release hardly functions or is markedly decreased when the drug is highly water-soluble. In WO98/10756, a method for coating with a polymer that can sustain release when water is used as the solvent, and a method for coating only with a heat-fused wax were attempted: latex of ethylcellulose, copolymer of ethyl acrylate and metacrylic acid, aminoalkyl methacrylate, etc. have been developed as polymers that can sustain release with an aqueous solvent, but even with these, it is difficult to control release of a highly water-soluble drug over a long time period, and it has been reported that the steady zero-order release of a drug is impossible even with a very thick film for the release controlling.

DISCLOSURE OF THE INVENTION

A primary object of the present invention is to provide sustained release micropellets and medicinal compositions containing the micropellets that realize stable control of release even when the drug is water-soluble, improve patients' compliance and QOL, and make it easier or possible to administer orally to the aged, children and even patients with decreased swallowing function.

A second object is to provide sustained release micropellets and medicinal compositions containing the micropellets that can be prepared by layering or coating without use of organic solvents and can be formulated in the form of suspension, paste, or syrup by addition of a suitable amount of water, solution, etc. as needed before administration.

The inventors have found, as the result of their researches to accomplish the above-mentioned objects, that controlled release micropellets showing stable sustained-release of a drug without being affected by changes in pH value, etc. can be obtained when a layer of a water-soluble filler, of which use for the sustained-release of a water-soluble drug has been considered generally unacceptable, is formed between the granulation product and the film layer in the sustained-release micropellets produced by coating core particles with a layer containing a water-soluble drug and further forming a film layer containing a water-insoluble polymer compound and a plasticizer on the particles. Thus the inventors have completed the invention.

The sustained release micropellets of the invention usually have an average particle size of 300 µm or less, desirably of 150 to 300 µm. These micropellets can be prepared by layering or coating using the conventionally used rolling granulating apparatus, fluidized bed coating apparatus, etc. The shape of micropellets is not particularly limited but desirably granular or globular shape.

The weight of the film layer containing a water-insoluble polymer compound and a plasticizer is desirably 20 to 50%, more desirably 25 to 40%, of the sum of the weight of the core particles coated with a layer of a water-soluble drug and the weight of the layer of a water-soluble filler. The film layer containing a water-insoluble polymer compound and a plasticizer is desirably composed of two or more layers including the film layer not containing the water-soluble polymer compound and the film layer containing the water-soluble polymer compound, and more desirably the film layer containing the water-soluble polymer compound is located outside the film layer not containing the water-soluble polymer compound. In the sustained release micropellets of the invention, the release control pattern appropriate for various water-soluble drugs or patients can be selected readily by changing the ratio of the film layer arbitrarily within the above-mentioned range or by mixing micropellets with a different ratio of film layers; even a pattern of controlling release of roughly zero order can be obtained. In such a case, release of a drug is more controlled by increasing the ratio of the film layer containing a water-insoluble polymer compound and a plasticizer, particularly the ratio of the film layer containing a water-insoluble polymer compound and a plasticizer but not containing a water-soluble polymer compound.

The water-soluble drugs of the present invention are not particularly limited, and include, for example, analgesics, anti-inflammatory agents, sympathomimetic agents, central nervous system-acting agents, cardiotonics, anti-allergic agents, anti-histamic agents, anti-hypertensive agents, antibiotics, anti-neoplastic agents, antiarrhythmic agents, vitamins, bronchodilating agents, etc.

Water-soluble drugs in this context mean those which require less than 1000 ml, preferably less than 500 ml, of water for dissolution of 1 g of the drug in the solubility test (degree of dissolution within 30 minutes at 20±5° C. while vigorously shaking for 30 seconds every 5 minutes) as described under Description, General Notices, the pharmacopoeia of Japan (JP), though the definition is not strict because it may vary depending on the unit dose. Among the above-mentioned water-soluble analgesics, especially desirable ones are opioid analgesics such as morphine, codeine, hydromorphone, methadone, meperidine, levorphanol, pethidine, tilidine, tramadol, fentanyl, buprenorphine, piritramide, and derivatives thereof, pharmaceutically acceptable salts thereof, and mixtures thereof. The invention is particularly useful for water-soluble analgesics, those that require 3 or more times administration per day when given at an appropriate dose, those that require administration during bed rest at night, and those with a short half-life in blood, representative examples of which are morphine, its derivatives, and its pharmaceutically acceptable salts.

Core particles used in the invention are those used for usual layering such as powder or crystalline cellulose, starch, sugar, etc. and not particularly limited as far as those by which sustained release micropellets of the invention having an average particle size of 300 µm or less can be obtained after specified layering and coating, the average particle size being desirably 100 to 250 µm and more desirably 150 to 200 µm. The shape of the particles is not particularly limited but desirably granular or globular.

Water-insoluble polymer compounds include cellulose esters such as ethylcellulose and butylcellulose, copolymers of acrylic acid/methyl methacrylate, etc., copolymers of ethyl methacrylate/aminoalkyl methacrylate, etc., analogues thereof, and mixtures thereof, and desirably cellulose esters, and more desirably ethylcellulose. Water-insoluble polymer compounds in this context are those that require not less than 10000 ml of water for dissolution of 1 g of the compound in the solubility test described above.

Plasticizers include triethyl citrate, tributyl citrate, triacetin, diethyl acetate, phthalate esters, and castor oil. The ratio of a plasticizer to a water-insoluble polymer compound is 10 to 50% by weight, desirably 15 to 35% by weight.

Water-soluble polymer compounds include hydroxypropylmethylcellulose, hydroxypropylcellulose, methylcellulose, sodium carboxymethylcellulose, polyethyleneglycol and water-soluble polysaccharides, among which hydroxypropylmethylcellulose is the most desirable. Water-soluble polymer compounds in this context are those 1 g of which is soluble in less than 10000 ml of water in the solubility test described above.

Fillers include oligosaccharides such as lactose, sucrose, D-mannitol, sorbitol, and glucose, polysaccharides such as dextrin, dextran and pullulan, starches such as corn starch, α-starch, and carboxymethyl starch, celluloses such as crystalline cellulose, crystalline cellulose carmellose sodium, and low substituted hydroxypropylmethylcellulose, silicic acids such as synthetic aluminum silicate and magnesium aluminometasilicate, inorganic acid salts such as calcium phosphate, calcium carbonate, and calcium sulfate, xanthan gum, acacia, etc. Fillers used in the layer of water-soluble filler are water-soluble fillers including oligosaccharides such as lactose, sucrose, mannitol, sorbitol, and glucose, water-soluble polysaccharides such as dextrin, acacia, and mixtures thereof, among which oligosaccharides are particularly desirable and lactose is further desirable. Water-soluble fillers in this context are those 1 g of which is soluble in less than 100 ml of water in the solubility test described above.

For formation of the layer of a water-soluble filler by layering or coating, the filler is desirably used as an almost saturated solution, a solution of a higher concentration, a dispersion, or a suspension in water or an aqueous solution to be used, and may contain an additive such as a binder described below as needed within the range of the conventional method.

Binders include polyvinylpyrrolidone, hydroxypropylmethylcellulose, hydroxypropylcellulose, methylcellulose, hydroxyethylcellulose, mixtures thereof, etc.; stabilizers include citric acid, tartaric acid, succinic acid, fumaric acid, maleic acid, sodium hydrogen sulfite, etc.; lubricants include light anhydrous silicic acid, talc, magnesium stearate, magnesium oxide, titanium oxide, etc. These compounds may be added and used as needed according to the conventional method.

The sustained release micropellets of the invention can be produced by layering and coating using water or an aqueous solution as the solvent without using any organic solvent, and can be formulated into medicinal compositions in the form of fine granules, powders, and dry syrups, according to the conventional method by addition of acceptable additives in the field of formulation, such as a filler, sweetening agent, flavoring agent, binder, disintegrator, suspending agent, perfume, artificial color, stabilizer, lubricant, etc. In addition, sustained release micropellets and medicinal compositions thereof of the invention can be filled in hard capsules or supplied as sub-packaging powder, etc.

BEST MODE FOR CARRYING OUT THE INVENTION

Figure 1:
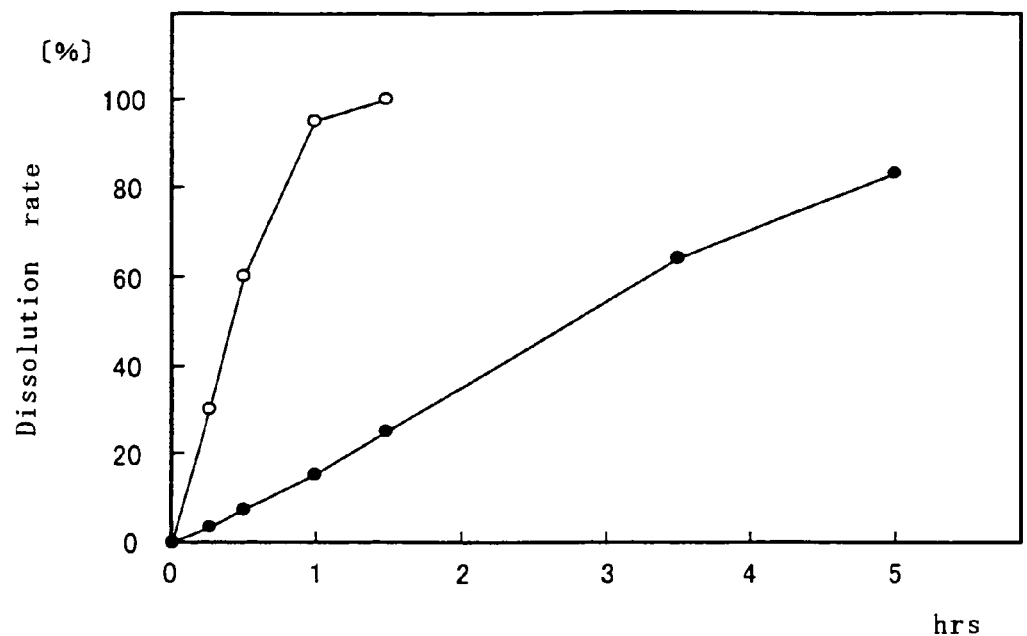
FIG. 1: Pattern of dissolution of morphine in Example 6.
"○": Dissolution pattern from sustained release micropellets of Example 2.
"●": Dissolution pattern from sustained release micropellets of Example 3.

The invention will be explained in detail in the following Examples, though the scope of the claimed invention is not limited only to these Examples.

Example 1

In a Teflon-coated rolling fluidized bed granulating-coating apparatus, with electrostatic protection as needed, 660 g of crystalline cellulose particles having an average particle size of not more than 200 μm was sprayed with an aqueous solution in which 330 g of morphine sulfate, 60 g of hydroxypropylcellulose, 8.3 g of citric acid, and 0.7 g of sodium hydrogen sulfite had been dissolved under the conditions of air supply of 20 to 40 $m^3$/hr, inlet air temperature of 77 to 83° C., outlet air temperature of 34 to 37° C., rotor rotation of 240 to 280 rpm, spray rate of 4 to 8 g/min, spray air pressure of 1.8 to 2.0 kg/$cm^2$, spray air volume of 25 to 30 L/min, side-air quantity of 60 to 70 L/min, followed by drying under the conditions of the air temperature of 45° C. at the outlet, to give a granulation product coated with a layer containing morphine sulfate. Then the granulation product was sprayed with an aqueous dispersion or suspension of 84 g of lactose and 7 g of hydroxypropylcellulose followed by drying, so that the granulation product was coated with a lactose layer.

Example 2

A portion of the granulation product coated with a lactose layer obtained in Example 1 was subjected to spray-coating in a rolling fluidized bed granulating-coating apparatus under the conditions of air supply of 35 to 55 $m^3$/hr, inlet air temperature of 77 to 83° C., outlet air temperature of 36 to 38° C., rotor rotation of 250 to 300 rpm, spray rate of 5 to 11 g/min, spray air pressure of 1.8 to 2.0 kg/$cm^2$, spray air volume of 25 to 30 L/min, side-air quantity of 60 to 70 L/min, and drying temperature of 54 to 56° C., with an aqueous dispersion/suspension of 120 g of ethylcellulose and 40 g of triethyl citrate so that the weight of solid ingredients became to be 10% of the weight of the granulation product coated with a lactose layer, and the coated product was dried. The product was further subjected to spray-coating with an aqueous dispersion/suspension of 115 g of ethylcellulose, 28 g of triethyl citrate, and 7 g of hydroxypropylmethylcellulose so that the weight of solid ingredients became to be 15% of the weight of the granulation product coated with a lactose layer, and the coated product was dried, to give sustained release micropellets having an average particle size of 300 μm or less.

Example 3

Another portion of the granulation product coated with a lactose layer obtained in Example 1 was subjected to spray-coating in the rolling fluidized bed granulating-coating apparatus under the same conditions as in Example 2 with an aqueous dispersion/suspension of 120 g of ethylcellulose and 30 g of triethyl citrate so that the weight of solid ingredients became to be 25% of the weight of the granulation product coated with a lactose layer, and the product was dried. The product was further subjected to spray-coating with an aqueous dispersion/suspension of 115 g of ethylcellulose, 28 g of triethyl citrate, and 7 g of hydroxypropylmethylcellulose so that the weight of solid ingredients became to be 10% of the weight of the granulation product coated with a lactose layer, and the product was dried, to give sustained release micropellets having an average particle size of 300 μm or less.

Example 4

Sustained release micropellets obtained in Example 2 and those in Example 3 were mixed at the ratio of 1:1, and 135 g of the resultant mixture (containing about 30 g of morphine sulfate), 832 g of lactose, 240 g of D-mannitol, 120 g of sucrose, 120 g of crystalline cellulose-carmellose sodium, 8 g of xanthan gum, and 8 g of sodium lauryl sulfate were charged in a rolling fluidized bed granulating-coating apparatus for spray-granulation with an aqueous solution containing 5 g of aspartame, 2 g of sodium chloride, and 3 g of citric acid and an aqueous solution containing 24 g of polyvinylpyrrolidone (K30) under the conditions of air supply of 40 to 50 m$^3$/hr, inlet air temperature of 80° C., outlet temperature of 34 to 37° C., rotor rotation of 240 to 280 rpm, spray rate of 4 to 8 g/min, spray air pressure of 1.8 to 2.0 kg/cm$^2$, spray air volume of 20 to 30 L/min, and air temperature of 45° C. at the outlet during drying, and the product was dried, followed by sizing the particles with a sieve after addition of 3 g of light anhydrous silicic acid, to give fine granules (dry syrup) containing 2% of morphine sulfate.

Example 5

Sustained release micropellets obtained in Example 2 and those in Example 3 were mixed at the ratio of 1:1, and 405 g of the resultant mixture (containing about 90 g of morphine sulfate), 640 g of lactose, 200 g of D-mannitol, 100 g of sucrose, 100 g of crystalline cellulose-carmellose sodium, 10 g of xanthan gum, and 6 g of sodium lauryl sulfate were charged in a rolling fluidized bed granulating-coating apparatus for spray-granulation with an aqueous solution containing 2 g of sodium chloride and 4 g of citric acid and an aqueous solution containing 30 g of polyvinylpyrrolidone (K30) under the same conditions as in Example 4, and the product was dried, followed by sizing the particles with a sieve after addition of 3 g of light anhydrous silicic acid, to give fine granules containing 6% of morphine sulfate (dry syrup), which was divided by 0.5 g per pouch by a powder-dividing and packaging machine. (0.5 g of the powder in a pouch contains 30 mg of morphine sulfate.)

Example 6

Sustained release micropellets obtained in Example 2 and those in Example 3 were separately subjected to determination of the dissolution rate of morphine by using water as the test solution at the paddle rate of 100 rpm as directed in the Method (2) under the Dissolution Test, General Tests of the Japanese Pharmacopoeia (JP). The dissolution patterns are illustrated in FIG. 1.

Example 7

Figure 2:
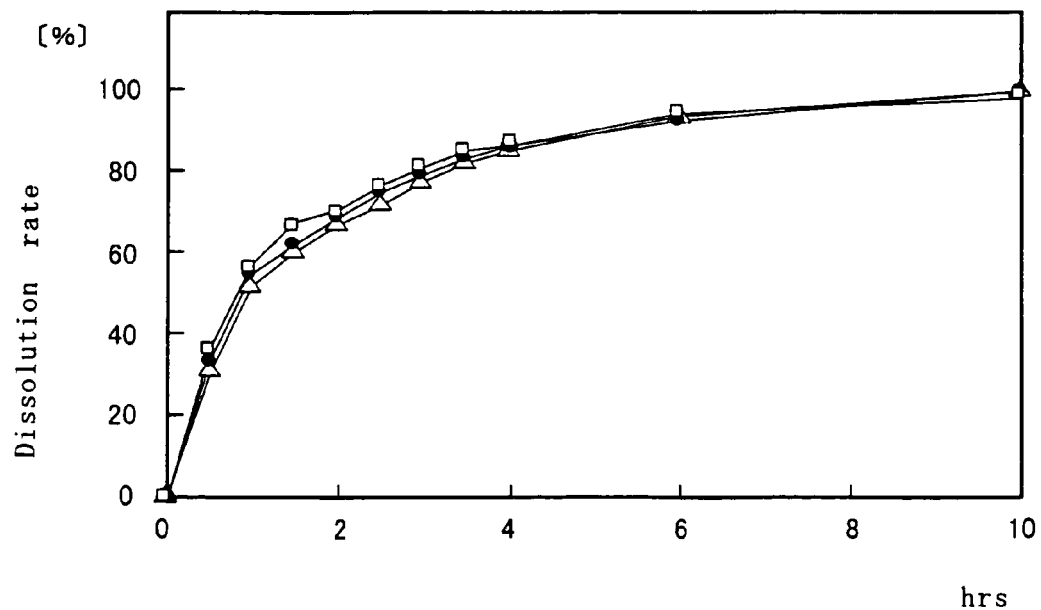
FIG. 2: Pattern of dissolution of morphine in Example 7.
"△": Paddle rate of 50 rotations per minute.
"●": Paddle rate of 100 rotations per minute.
"□": Paddle rate of 200 rotations per minute.

Fine granules (dry syrup) obtained in Example 4 were subjected to determination of the dissolution rate of morphine by using water as the test solution at the paddle rate of 50, 100 or 200 rpm as directed in the Method (2) under the Dissolution Test, General Tests, JP. The dissolution patterns are illustrated in FIG. 2.

Example 8

Figure 3:
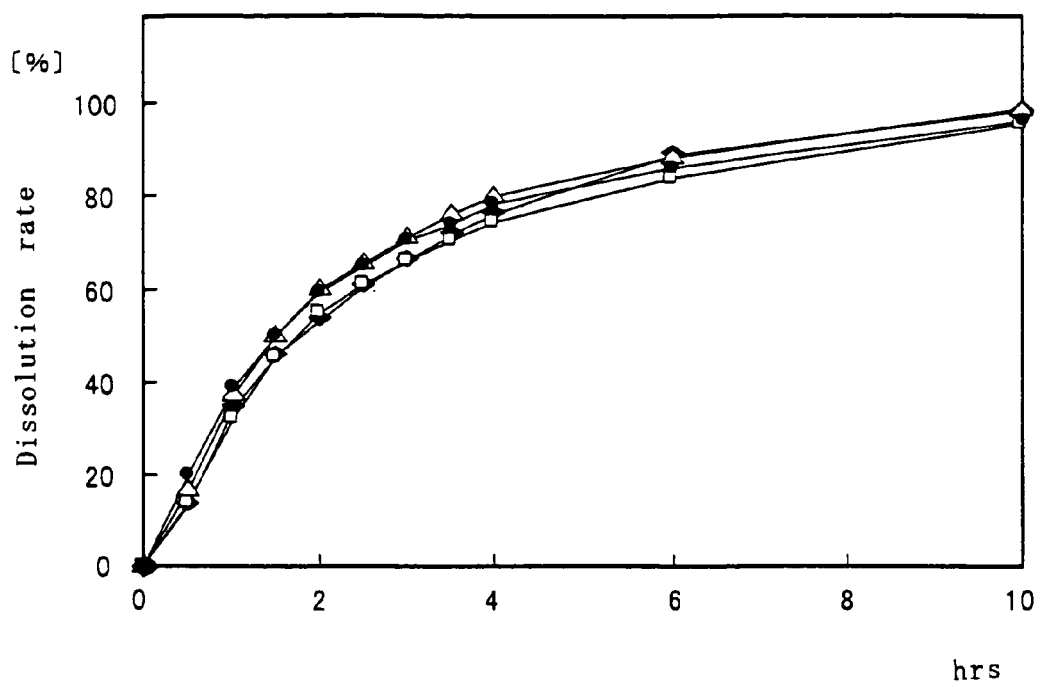
FIG. 3: Pattern of dissolution of morphine in Example 8.
"◆": pH 1.2, "△": pH4.0, "□":pH6.8, "●": water.

Fine granules (dry syrup) obtained in Example 5 were subjected to determination of the dissolution rate of morphine by using a solution of pH1.2, pH4.0, pH6.8 or water as the test solution at the paddle rate of 50 rpm as directed in the Method (2) under the Dissolution Test, General Tests of JP. The dissolution patterns are illustrated in FIG. 3

INDUSTRIAL APPLICABILITY

Sustained release micropellets of the present invention having an average particle size of 300 μm or less and medicinal compositions containing these sustained release micropellets have a stable release-controlling action without being affected by pH, etc., and make oral administration or nasogastric tube-administration easy or possible in children, the aged, and even in patients with decreased swallowing function, when administered as they are or after formulation into suspension, paste, or syrup by addition of an appropriate amount of water, an aqueous solution, etc. before administration as needed. The basic unit that shows sustained release is a small particle and it is possible to change arbitrarily the ratio of the film layer within the specified range or to mix the preparations with different ratios of the film layer, so that the micropellets are suitable for improvement of patient's compliance and QOL because the dose of a drug and the control pattern can be adjusted even when the necessary amount varies depending on the difference in sensitivity, tolerance, or progress of the disease, etc. In addition, the sustained release micropellets, being able to be produced by layering and coating using water or an aqueous solution as the solvent, have no adverse effect on the environment due to residue, flammability, waste gas, etc. of an organic solvent. Thus the present micropellets have many advantages also in the process for production.

The invention claimed is:

1. A sustained release micropellet having an average particle size of 300 μm or less, which comprises a drug-free core particle (a) directly coated with a layer (b) containing a water-soluble drug, a water-soluble filler layer (c) formed thereon, and further a film layer (d) containing a water-insoluble polymer compound and a plasticizer formed thereon, wherein the film layer (d) is composed of two layers comprising an inner film layer (d-1) not containing any water-soluble polymer compound and an outer film layer (d-2) containing a water-soluble polymer compound.

2. The sustained release micropellet according to claim 1, wherein the weight of the film layer (d) is 20 to 50% of the total weight of the drug-free core particle (a) coated with the layer (b) containing a water-soluble drug and the water-soluble filler layer (c).

3. The sustained release micropellet according to claim 1, wherein the water-soluble drug in the layer (b) is a water-soluble analgesic and the water-insoluble polymer compound in the layer (d) is ethylcellulose.

4. The sustained release micropellet according to claim 3, wherein the water-soluble analgesic is an opioid analgesic.

5. The sustained release micropellet according to claim 4, wherein the opioid analgesic is morphine or a pharmaceutically acceptable salt thereof.

6. A medicinal composition comprising the sustained release micropellet according to claim 1, and an additive selected from the group consisting of a filler, a sweetening agent, a flavoring agent, a binder, a disintegrator, a suspending agent, a perfume, an artificial color, a stabilizer and a lubricant.

7. The medicinal composition according to claim 6, wherein the medicinal composition comprises two types of sustained release micropellets with different dissolution patterns.

8. The medicinal composition according to claim 6, wherein the medicinal composition is in the form of fine a granule, a powder or a dry syrup.

9. The medicinal composition according to claim 7, wherein the medicinal composition is in the form of fine a granule, a powder or a dry syrup.

10. A medicinal composition comprising the sustained release micropellet according to claim 2, and an additive selected from the group consisting of a filler, a sweetening agent, a flavoring agent, a binder, a disintegrator, a suspending agent, a perfume, an artificial color, a stabilizer and a lubricant.

11. The medicinal composition according to claim 10, wherein the medicinal composition comprises two types of sustained release micropellets with different dissolution patterns.

12. The medicinal composition according to claim 10, wherein the medicinal composition is in the form of fine a granule, a powder or a dry syrup.

13. The medicinal composition according to claim 11, wherein the medicinal composition is in the form of fine a granule, a powder or a dry syrup.

14. A medicinal composition comprising the sustained release micropellet according to claim 3, and an additive selected from the group consisting of a filler, a sweetening agent, a flavoring agent, a binder, a disintegrator, a suspending agent, a perfume, an artificial color, a stabilizer and a lubricant.

15. The medicinal composition according to claim 14, wherein the medicinal composition comprises two types of sustained release micropellets with different dissolution patterns.

16. The medicinal composition according to claim 14, wherein the medicinal composition is in the form of fine a granule, a powder or a dry syrup.

17. The medicinal composition according to claim 15, wherein the medicinal composition is in the form of fine a granule, a powder or a dry syrup.

18. A medicinal composition comprising the sustained release micropellet according to claim 4, and an additive selected from the group consisting of a filler, a sweetening agent, a flavoring agent, a binder, a disintegrator, a suspending agent, a perfume, an artificial color, a stabilizer and a lubricant.

19. The medicinal composition according to claim 18, wherein the medicinal composition comprises two types of sustained release micropellets with different dissolution patterns.

20. The medicinal composition according to claim 18, wherein the medicinal composition is in the form of fine a granule, a powder or a dry syrup.

21. The medicinal composition according to claim 19, wherein the medicinal composition is in the form of fine a granule, a powder or a dry syrup.

22. A medicinal composition comprising the sustained release micropellet according to claim 5, and an additive selected from the group consisting of a filler, a sweetening agent, a flavoring agent, a binder, a disintegrator, a suspending agent, a perfume, an artificial color, a stabilizer and a lubricant.

23. The medicinal composition according to claim 22, wherein the medicinal composition comprises two types of sustained release micropellets with different dissolution patterns.

24. The medicinal composition according to claim 22, wherein the medicinal composition is in the form of fine a granule, a powder or a dry syrup.

25. The medicinal composition according to claim 23, wherein the medicinal composition is in the form of fine a granule, a powder or a dry syrup.

26. A process for producing a sustained release micropellet having an average particle size of 300 μm or less, which comprises directly coating a drug-free core particle (a) with a layer (b) containing a water-soluble drug, forming a water-soluble filler layer (c) thereon, and further forming a film layer (d) containing a water-insoluble polymer compound and a plasticizer thereon, wherein the film layer (d) is composed of two layers comprising an inner film layer (d-1) not containing any water-soluble polymer compound and an outer film layer (d-2) containing a water-soluble polymer compound thereon.

27. The process for producing the sustained release micropellet according to claim 26, wherein the layer containing a water-soluble drug (b), the water-soluble filler layer (c) and the film layer (d) containing a water-insoluble polymer compound and a plasticizer are formed by layering or coating using water or an aqueous solution as a solvent.

* * * * *